(12) United States Patent
Pellegrino et al.

(10) Patent No.: US 7,383,719 B1
(45) Date of Patent: Jun. 10, 2008

(54) AUTOMATED PASSENGER SCREENING SYSTEM

(75) Inventors: Francesco Pellegrino, Cold Spring Harbor, NY (US); Matthew R. Shapiro, Llyod Harbor, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 188 days.

(21) Appl. No.: 11/465,482

(22) Filed: Aug. 18, 2006

Related U.S. Application Data

(60) Provisional application No. 60/710,829, filed on Aug. 24, 2005.

(51) Int. Cl.
*G01N 1/04* (2006.01)
(52) U.S. Cl. .................................. 73/28.04; 73/864.41
(58) Field of Classification Search ............. 73/864.41, 73/864.81, 28.04
See application file for complete search history.

(56) References Cited

U.S. PATENT DOCUMENTS

| | | | | | |
|---|---|---|---|---|---|
| 2,895,159 | A | * | 7/1959 | Ostrow ........................ | 15/311 |
| 3,044,099 | A | * | 7/1962 | Scott et al. ................... | 15/311 |
| 4,233,707 | A | * | 11/1980 | Leblanc ....................... | 15/311 |
| 6,067,688 | A | * | 5/2000 | West ........................... | 15/311 |
| 2004/0222790 | A1 | * | 11/2004 | Karmi et al. ............... | 324/300 |
| 2007/0086925 | A1 | * | 4/2007 | O'Donnell et al. ......... | 422/100 |

* cited by examiner

*Primary Examiner*—Hezron E. Williams
*Assistant Examiner*—Tamiko D Bellamy
(74) *Attorney, Agent, or Firm*—DeMont & Breyer LLC

(57) ABSTRACT

A screening system for screening passengers is disclosed. The system includes a floor grating having underlying rotating brushes that are installed in access ways at public venues (e.g., doors, turnstiles, escalators, etc.). As each passenger steps on the grating, the rotating brushes remove traces of material from the soles of that passenger's shoes and the material is analyzed for the presence of CBRNE agents via appropriate local detectors.

14 Claims, 2 Drawing Sheets

AUTOMATED PASSENGER SCREENING SYSTEM

STATEMENT OF RELATED CASES

This case claims the benefit of U.S. provisional patent application 60/710,829, which was filed on Aug. 24, 2005 and is incorporated by reference herein.

FIELD OF THE INVENTION

The present invention relates to homeland security, and more particularly to a system that screens individuals for the presence of chemical, biological, radiological, nuclear, and explosive ("CBRNE") materials, or other potentially hazardous or lethal materials.

BACKGROUND OF THE INVENTION

Terrorism is on the rise. A favorite target of terrorists is the public transportation systems: air, rail, bus, etc. For example, in a recent incident abroad, terrorists carried explosives onto buses and subways and detonated or attempted to detonate them. Many people were killed or wounded.

The most intense screening of passengers presently occurs at airports. Passengers are screened for the presence of metals and luggage is examined by x-ray analysis. In some installations, passengers are screened for the presence of explosives by passing air over their clothing in an attempt to extract traces of chemicals that are indicative of explosives. The air is then analyzed by a local detector. This requires the isolation and screening of individual passengers, which results in high unit screening cost and passenger traffic delays. Additionally, explosives can (and have been) hidden in shoes, which are usually independently screened by airport screeners.

The challenge is: how to prevent weapons-laden terrorists from accessing public transportation systems without substantially slowing the movement of individuals into these systems? And how to do so in a cost-effective manner.

SUMMARY OF THE INVENTION

The present invention provides a way to screen passengers for the presence of CBRNE materials and other potentially harmful materials, without some of the costs and disadvantages of the prior art.

It is notable that while individuals change most of their clothes frequently (e.g., once per day, etc.), shoes, in particular, might be changed far less frequently. To the extent that an individual is preparing, over the course of a few days or more, an explosive device or other weapon that incorporates chemical, biological or radiological materials, the shoes of that individual are likely to have been exposed to such materials. Shoes, therefore, serve as an efficient collector of all contaminants that an individual is exposed to over a relatively extended period of time.

In accordance with the illustrative embodiment of the invention, a screening system includes a metal grating and rotating brushes that are installed in access ways at public venues (e.g., doors, turnstiles, escalators, etc.). As each passenger steps on the grating, the rotating brushes remove traces of material from the soles of that passenger's shoes and deposit it in an underlying collection container. The collected sample is tested for the presence of CBRNE agents via appropriate local detectors. A video camera identifies the individual whose trace results in an alarm.

Collection and analysis should require no more than several seconds, so that the system can be transparent to passengers when it is located at an access way that normally entails a very brief delay before entry. A turnstile, for example, is ideal for this purpose. Individuals must pass one at a time through the turnstiles at a relatively slow rate of speed. During high traffic periods, there is normally a short queue of passengers waiting to enter the turnstiles. Thus, the system can be positioned just before or at the turnstiles.

DETAILED DESCRIPTION

Figure 1:
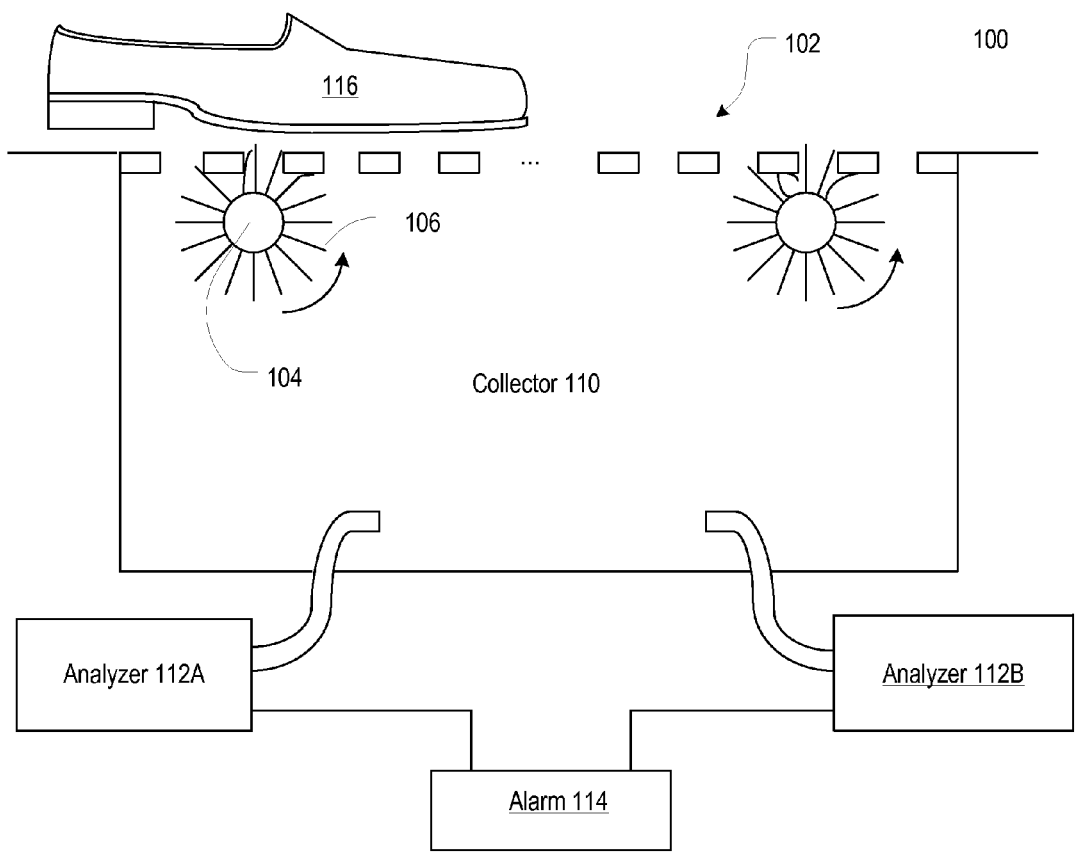
FIG. 1 depicts a side view of an automated passenger screening system in accordance with the illustrative embodiment of the present invention.

FIG. 1 depicts screening system 100 in accordance with the illustrative embodiment of the present invention. Screening system 100 includes grating 102, rotating brushes 104, collector 110, and analyzers 112, alarm device 114, arranged as shown.

As depicted in FIG. 1, brushes 104 are disposed beneath grating 102. Bristles 106 extend slightly beyond upper surface 108 of grating 102. Motors (not depicted) drive brushes 104 into rotation at a relatively high rate of speed. When shoe 116 comes into contact with upper surface 108 of grating 102, bristles 106 swipe the underside of the shoe, dislodging small particulates, dust, etc., from the shoe. These particulates drop into collector 110. One or more local analyzers 112A, 112B analyze the particulates in collector 110.

If the concentration of a certain particulates (i.e., those indicative of CBRNE materials) exceed set thresholds for such particulates, alarm device 114 is activated (e.g., siren, lights, etc.) and appropriate action is taken to detain the individual that is responsible for the alarm. After an alarm is triggered, grating 102, brushes 104, and collector 110 are changed out and analyzers 112A and 112B are purged, as required. Since alarms are expected (and hoped!) to be a very infrequent occurrence, this change-out procedure should not be unduly burdensome.

Figure 2:
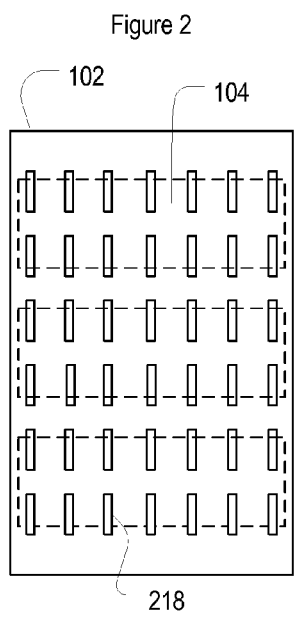
FIG. 2 depicts a top view of a first grating suitable for use in the screening system of FIG. 1.
Figure 3:
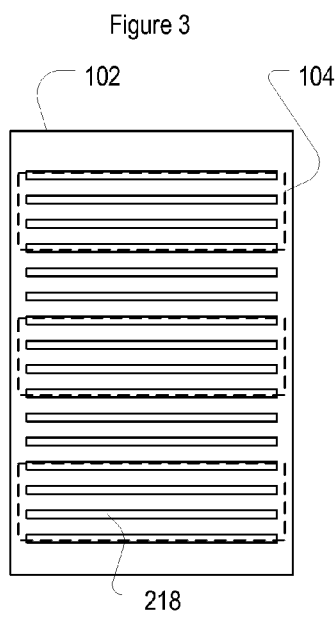
FIG. 3 depicts a top view of a second grating suitable for use in the screening system of FIG. 1.

FIGS. 2 and 3 depict top views of two embodiments of grating 102. As depicted in FIGS. 2 and 3, grating 102 comprises a plurality of narrow slits 218 through which particulate samples are obtained. The slits can be situated either parallel (FIG. 2) or orthogonal (FIG. 3) to the direction of movement of screened individuals. The slits can be discontinuous, as depicted in FIG. 2, or continous, as depicted in FIG. 3. (And, of course, discontinuous slits can be used with either parallel or orthogonal-oriented slits; likewise for continuous slits.)

Slits 218 are typically about ¼ to ¹⁄₁₆ inch wide. Brushes 104 must be sufficient in number and size to ensure that where ever a person steps on grating 102, a sample will be obtained from that person's shoe. Bristles 106 must be suitably stiff and robust (e.g., nylon, etc.) to withstand repeated contact with the soles of shoes 116. And, of course, the grating should be large enough to ensure that each person passing the grating will step on it, thereby assuring that a screening will occur. A grating having a size of at least about 3 feet×2 feet should be adequate for this purpose.

Figure 4:
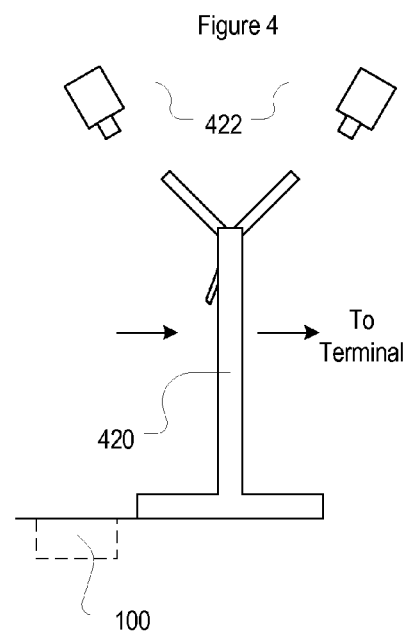
FIG. 4 depicts the screening system of FIG. 1 installed "upstream" of a passenger turnstile.

FIG. 4 depicts screening system 100 installed directly before a turnstile 420 that controls the movement of passengers into a public transportation terminal. Cameras 422 obtain images of passengers as they pass through turnstile 420, and are used to identify a person that sets off an alarm. In some embodiments, the camera runs continually, while in some other embodiments, the cameras activate when an individual passes a sensor (not depicted) that is located before grating 102, when an individual steps on grating 102, or as an individual passes through turnstile 420. In some further embodiments, cameras 422 activate when an alarm is sounded.

Screening system 100 is large enough to ensure that each person that passes through turnstile 420 must step on grating 102. If there is a queue of passengers waiting to pass turnstile 420, there will be plenty of time to obtain a sample from the shoes and analyze it. (Obtaining the sample and analyzing it should require only a few seconds.)

In cases in which there is no line of people waiting to pass through turnstile 420, the brief pause that individuals typically make before entering a turnstile should provide sufficient time for the system to obtain and analyze a sample before the lone passenger clears turnstile 420. In any event, in the absence of passengers except for the one that sets off an alarm, identifying that passenger will be a simple matter.

It is to be understood that the above-described embodiments are merely illustrative of the present invention and that many variations of the above-described embodiments can be devised by those skilled in the art without departing from the scope of the invention. For example, in this Specification, numerous specific details are provided in order to provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the specification to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Specification are not necessarily all referring to the same embodiment. Furthermore, the particular features, structures, materials, or characteristics can be combined in any suitable manner in one or more embodiments. It is therefore intended that such variations be included within the scope of the following claims and their equivalents.

What is claimed:

1. A screening system comprising:
   a grating, wherein said grating is installed in a floor;
   a brush, wherein said brush is disposed underneath said grating, and wherein said brush is operative to dislodge particulates from a sole of a shoe that contacts said grating;
   a collector, wherein said collector collects said particulates that are dislodged from said sole of said shoe; and
   an analyzer for analyzing said particulates.

2. The system of claim 1 wherein said brush rotates.

3. The system of claim 1 wherein said analyzer is capable of detecting explosives.

4. The system of claim 1 wherein said analyzer is selected from the group consisting of an explosives detector, a chemical detector, a biological detector, and a radiological detector.

5. The system of claim 1 further comprising a device capable of issuing an alarm, wherein said alarm issues if said analyzer detects the presence of a species of interest.

6. The system of claim 1 further comprising a video camera, wherein said video camera is positioned to obtain an image of a person who steps on said grating.

7. The system of claim 5 further comprising a video camera, wherein said video camera is positioned to obtain an image of a person who is responsible for issuance of said alarm.

8. The system of claim 1 further comprising a device to regulate a flow of people into an area, wherein said screening system is disposed before said device.

9. The system of claim 8 wherein said device is a turnstile.

10. A screening system comprising:
    a passenger flow-control device for regulating a flow of persons into an area;
    a grating, wherein said grating is installed in a floor before said flow-control device;
    a brush, wherein said brush is disposed underneath said grating, and wherein said brush is operative to dislodge particulates from a sole of a shoe of a person that steps on said grating before entering said flow-control device; and
    an analyzer for analyzing said particulates.

11. The screening system of claim 10 further comprising a video camera for obtaining an image of a person that steps on said grating.

12. The screening system of claim 10 further comprising a device capable of issuing an alarm, wherein said alarm issues if said analyzer detects the presence of a species of interest in excess of a threshold level.

13. The screening system of claim 12 further comprising a video camera for obtaining an image of a person that is responsible for issuance of said alarm.

14. The screening system of claim 10 wherein said analyzer is selected from the group consisting of an explosives detector, a chemical detector, a biological detector, and a radiological detector.

* * * * *